United States Patent [19]

Arrowsmith et al.

[11] Patent Number: 4,822,793
[45] Date of Patent: Apr. 18, 1989

[54] BENZAZEPINE ANTIARRHYTHMIC AGENTS

[75] Inventors: John E. Arrowsmith, Deal; Peter E. Cross, Canterbury, both of England

[73] Assignee: Pfizer Inc., New York, N.Y.

[21] Appl. No.: 170,487

[22] Filed: Mar. 21, 1988

[30] Foreign Application Priority Data

Mar. 25, 1987 [GB] United Kingdom ............... 8707121

[51] Int. Cl.$^4$ ..................... A61K 31/33; C07D 223/16
[52] U.S. Cl. ..................................... 514/213; 540/594
[58] Field of Search ..................... 540/594; 514/213

[56] References Cited

FOREIGN PATENT DOCUMENTS 0164865 12/1985 European Pat. Off. ............ 540/594

Primary Examiner—Mary C. Lee
Assistant Examiner—Robert C. Whittenbaugh
Attorney, Agent, or Firm—Peter C. Richardson; Paul H. Ginsburg; Lawrence C. Akers

[57] ABSTRACT

Compounds of the formula:

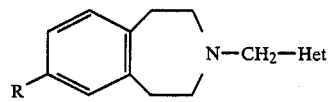

(A)

or a salt thereof, wherein "Het" is a group of the formula:

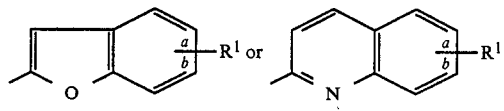

in which $R^1$ is attached to position "a" or "b" of the benzene ring and R and $R^1$, which are the same, are —NHSO$_2$(C$_1$–C$_4$ alkyl), —NH$_2$ or —NO$_2$.

The compounds in which R and $R^1$ are —NHSO$_2$(C$_1$–C$_4$ alkyl) are cardiac antiarrhythmic agents. The compounds in which R and $R^1$ are —NO$_2$ and —NH$_2$ are synthetic intermediates.

13 Claims, No Drawings

BENZAZEPINE ANTIARRHYTHMIC AGENTS

This invention relates to certain benzazepine sulfonamides which are antiarrhythmic agents, and to intermediates therefor.

The antiarrhythmic compounds of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

Thus the invention provides compounds of the formula:

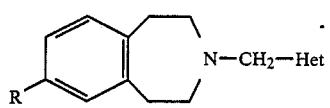
(A)

and their salts, wherein "Het" is a group of the formula:

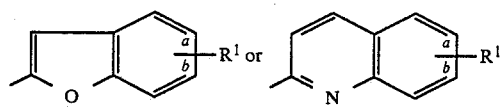

in which $R^1$ is attached to position "a" or "b" of the benzene ring; and R and $R^1$, which are the same, are both —$NO_2$, —$NH_2$ or —$NHSO_2(C_1$-$C_4$ alkyl).

The compounds of the formula (A) in which R and $R^1$ are both —$NHSO_2(C_1$-$C_4$ alkyl) are antiarrhythmic agents. The compounds of the formula (A) in which R and $R^1$ are both —$NO_2$ or —$NH_2$ are synthetic intermediates.

Thus the invention provides antiarrhythmic agents of the formula:

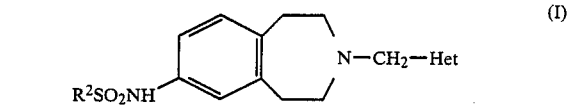
(I)

and their pharmaceutically acceptable salts, wherein "Het" is a group of the formula:

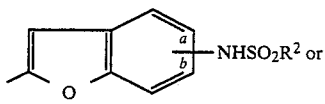

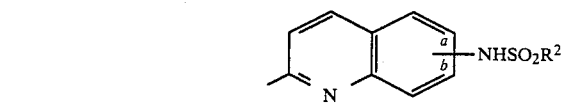

and each $R^2$, which is the same, is a $C_1$-$C_4$ alkyl group, the group —$NHSO_2R^2$ in "Het" being attached to position "a" or "b" of the benzene ring.

The preferred alkyl group is methyl.

$R^1$ is preferably attached to position "a" of the benzene ring portion of the heterocycle.

The compounds will be named as derivatives of 1,2,4,5-tetrahydro-3H-3-benzazepine which has the formula:

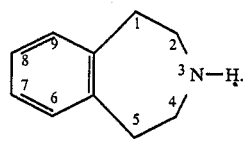

The compounds of the formula (I) can be prepared by the acylation of the compounds of the formula (A) in which both R and $R^1$ are —$NH_2$. The acylation can be carried out conventionally with a $C_1$-$C_4$ alkanesulphonic anhydride or $C_1$-$C_4$ alkanesulphonyl chloride or bromide in a suitable organic solvent, e.g. methylene chloride or pyridine, typically at room temperature. The presence of an acid acceptor such as triethylamine, sodium or potassium carbonate, or pyridine is desirable. It is in fact preferred to carry out the acylation in pyridine which functions both as the solvent and the acid acceptor. The product of the formula (I) can then be isolated and purified conventionally.

The starting materials for this process, i.e. the compounds of the formula (A) in which R and $R^1$ are both —$NH_2$, can be prepared by the reduction of the corresponding di-nitro compounds using, e.g., $H_2$/Pd/C in conventional manner. The starting materials of the formula (A) in which R and $R^1$ are both —$NO_2$ can in turn be prepared as follows:

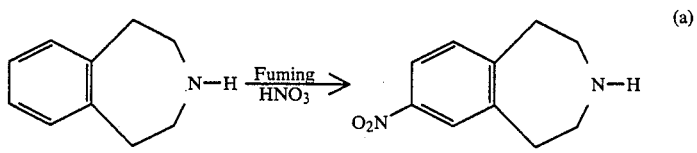
(a)

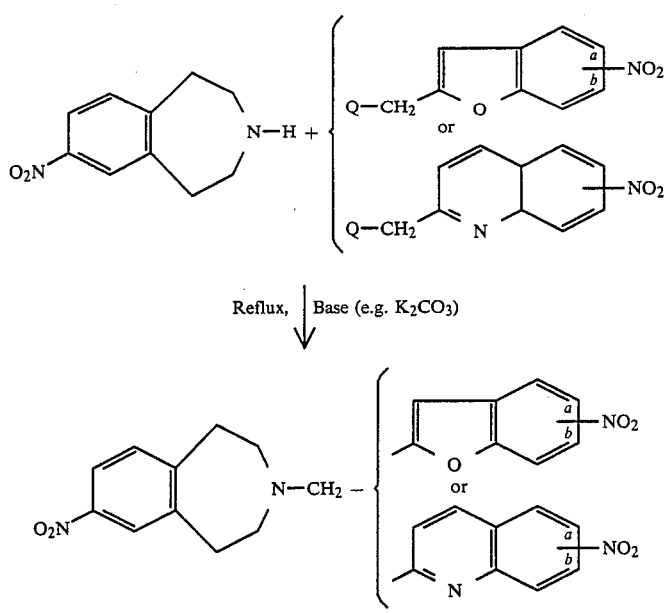

Q is a leaving group such as Cl, Br, I, methanesulphonyloxy, benzenesulphonyloxy or toluenesulphonyloxy. Preferably Q is Cl or Br and the reaction is carried out in a suitable organic solvent, e.g. acetonitrile, at reflux in the presence of sodium iodide (catalyst) and potassium carbonate.

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. The compounds also form metal salts, preferred examples of which are the alkaline earth and alkali metal salts. The sodium and potassium salts are most preferred. The salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 1 to 75 mg daily, taken in up to 4 divided doses per day, for an average adult patient (70 kg). Dosages for intravenous administration would be expected to be within the range 0.5 to 10 mg per single dose as required. A severe cardiac arrythmia is preferably treated by the i.v. route in order to effect a rapid conversion to the normal rhythm. Thus for a typical adult patient individual tablets or capsules might for example contain 1 to 25mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly as an antiarrhythmic agent.

The invention also provides the use of a compound of the formula (I), or of a pharmaceutically acceptable salt thereof, for the manufacture of a medicament for the prevention or reduction of cardiac arrhythmias.

The following Examples, in which all temperatures are in °C., illustrate the preparation of the compounds of the formula (I):

EXAMPLE 1

7-Methanesulphonamido-3-(5-methanesulphonamidobenzofur-2-yl-methyl)-1,2,4,5-tetrahydro-3H-3-benzazepine

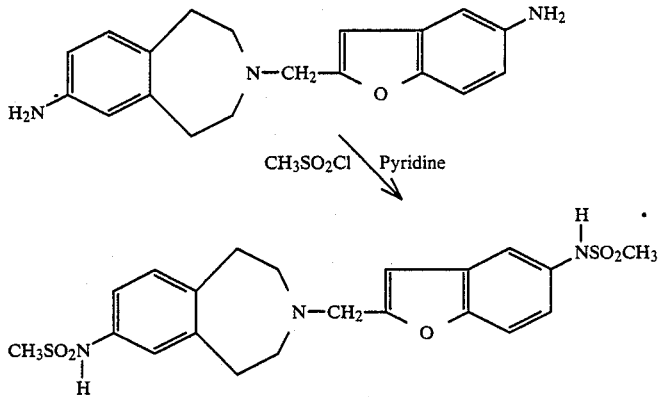

Methanesulphonyl cloride (0.28 ml) was added dropwise to a solution of 7-amino-3-(5-aminobenzofur-2-ylmethyl)-1,2,4,5-tetrahydro-3H-3-benzazepine (0.56 g) in pyridine (40 ml) cooled to 0° and the mixture was then stirred at room temperature for 18 hours. The solvent was evaporated in vacuo and the residue taken up in methylene chloride, washed three times with aqueous sodium bicarbonate and three times with brine. The organic layer was dried ($Na_2SO_4$), filtered and evaporated in vacuo to give an oil which was purified by column chromatography on silica eluting with methylene chloride containing methanol (0% up to 4%). The product-containing fractions were combined and evaporated to give the title compound as a foam, yield 0.56 g.

Analysis %: Found: C,50.5; H,5.2; N,8.1; Calculated for $C_{21}H_{25}N_3O_5S_2.\frac{1}{4}$ $H_2O.\frac{1}{2}CH_2Cl_2$*:C,50.6; H,5.2; N,8.2.

*The end product was found to be a solvate with $\frac{1}{2}$ a mole of methylene chloride as detected and quantified by 'H-n.m.r.

'H-N.m.r. ($CDCl_3$): $\delta=7.55$ (s, 1H); 7.5 (d, 1H); 7.15 (q, 1H); 7.1 (d, 1H); 7.0 (s, 2H); 6.8 (br s, 1H); 6.7 (br s, 1H); 6.6 (s, 1H); 3.9 (s, 2H); 3.0 (s, 6H); 2.95 (m, 4H); 2.75 (m, 4H).

EXAMPLE 2

7-Methanesulphonamido-3-(6-methanesulphonamidoquinol-2-ylmethyl)-1,2,4,5-tetrahydro-3H-3-benzazepine The title compound, m.p. 207°–210°, was prepared similarly to the procedure of Example 1 starting from 7-amino-3-(6-aminoquinol-2-ylmethyl)-1,2,4,5-tetrahydro-3H-3-benzazepine and methanesulphonyl chloride in pyridine.

Analysis %: Found: C,54.4; H,5.5; N,11.5; Calculated for $C_{22}H_{26}N_4O_4S_2.\frac{1}{2}H_2O$: C,54.3; H,5.6; N,11.5.

'H-N.m.r. (DMSO $d_6$) $\delta=8.3$ (d, 1H); 7.9 (d, 1H); 7.7 (s, 1H); 7.65 (d, 1H); 7.55 (d, 1H); 7.05 (d, 1H); 6.95 (s, 1H); 6.95 (d, 1H); 3.95 (s, 2H); 3.05 (s, 3H); 2.9 (s, 3H); 2.8 (m, 4H); 2.6 (m, 4H).

The following Preparations illustrate the preparation of certain of the starting materials used in the previous Examples. All temperatures are in °C.:

Preparation 1

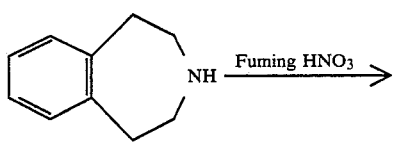

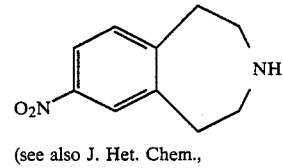

(see also J. Het. Chem., p. 779, vol. 8, 1971)

7-Nitro-1,2,4,5-tetrahydro-3H-3-benzazepine 1,2,4,5-Tetrahydro-3H-3-benzazepine (1 g) (see P. Ruggli et al., Helv. Chem. Acta, 18, 1388 [1935]) was added slowly, dropwise to stirred fuming nitric acid (25 ml, density 1.5 gm/ml) cooled to −10°. Stirring was continued at −10° for 1 hour, and the reaction mixture was then poured onto ice, the precipitate collected by filtration and dried to give the title compound as the nitrate salt, yield 1.4 g. A sample was recrystallised from water, m.p. 203°–204°.

Analysis %: Found: C,46.9; H,5.4; N,16.6; Calculated for $C_{10}H_{12}N_2O_2.HNO_3$: C,47.05; H,5.1; N,16.5.

The bulk of the nitrate salt was suspended in water, chilled and neutralised with 5M sodium hydroxide and the precipitate collected by filtration, recrystallised from water and dried to give the title compound, yield 0.6 g, m.p. 53°–56°.

Analysis %: Found: C,62.9; H,6.45; N,14.8. Calculated for $C_{10}H_{12}N_2O_2$: C,62.5; H,6.3; N,14.6.

Preparation 2

(A) 4-(Isopropylideneaminoxy)nitrobenzene

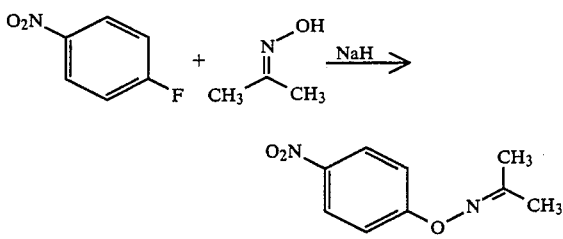

A solution of propanone oxime (30 g, 0.4 mole) in dry tetrahydrofuran (300 ml) was added slowly to a suspension of sodium hydride (10.8 g, 0.45 mole) in dry tetrahydrofuran (50 ml). After gas evolution was complete, dimethylsulphoxide (100 ml) and 4-fluoronitrobenzene (57.85 g, 0.41 mole) were added and the reaction mixture was stirred at room temperature for 2 hours. The reaction mixture was then poured into water and extracted three times with ether. The combined ether extracts were washed with water, dried (MgSO₄) and evaporated to give the title compound which was granulated in hexane and filtered, yield 67 g. A sample (7 g) was recrystallised from ethanol, yield 5 g, m.p. 104°–106°.

Analysis %: Found: C,55.6; H,5.05; N,14.35; Calculated for $C_9H_{10}N_2O_3$: C,55.7; H,5.2; N,14.4.

(B) 2-Methyl-5-nitrobenzofuran

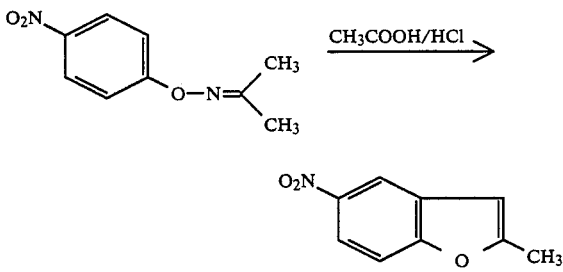

4-(Isopropylideneaminoxy)nitrobenzene (60 g, 0.309 mole) was added to glacial acetic acid (530 ml) containing gaseous hydrogen chloride (25 g) and the mixture was heated at 100° for 18 hours. The solvent was evaporated and the residue azeotroped with cyclohexane to give an oil which was diluted with water and extracted three times with methylene chloride. The combined organic extracts were washed with 10% aqueous sodium hydroxide solution and water, dried (MgSO₄) and evaporated to give the title compound, yield 46 g. A sample (5 g) was recrystallised from isopropanol, yield 2.5 g, m.p. 93°–95°.

Analysis %: Found: C,61.2; H,4.1; N,7.9; Calculated for $C_9H_7NO_3$: C,61.0; H,4.0; N,7.9.

(C) 2-Bromomethyl-5-nitrobenzofuran

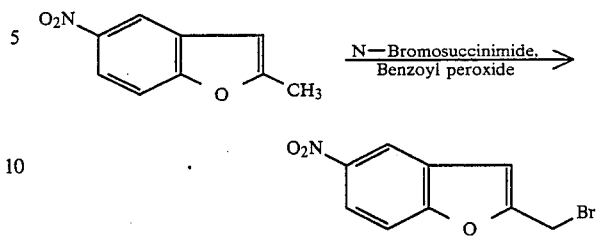

N-Bromosuccinimide (1.1 g, 6.2 mmole) was added portionwise to a solution of 2-methyl-5-nitrobenzofuran (1.0 g, 5.6 mmole) and benzoyl peroxide (50 mg) in carbon tetrachloride (50 ml) and the reaction mixture was heated at reflux temperature for 6 hours in the presence of bright light. The reaction mixture was then cooled, filtered and the filtrate evaporated to dryness. The residue was recrystallised from petroleum ether to give the title compound, yield 0.75 g, m.p. 96°–98°.

Analysis %: Found: C,41.7; H,2.4; N,5.3; Calculated for $C_9H_6BrNO_3$: C,42.2; H,2.4; N,5.5

Preparation 3

7-Nitro-3-(5-nitrobenzofur-2-ylmethyl)-1,2,4,5-tetrahydro-3H-3-benzazepine

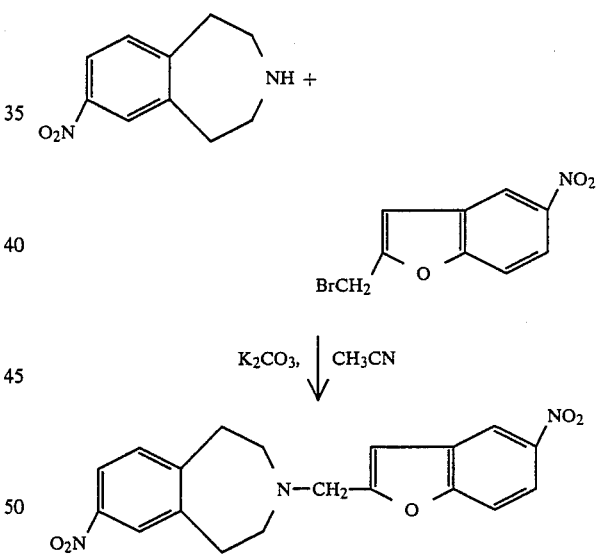

7-Nitro-1,2,4,5-tetrahydro-3H-3-benzazepine (0.7 g), 2-bromomethyl-5-nitrobenzofuran (0.93 g) and potassium carbonate (0.5 g) in acetonitrile were heated under reflux for 8 hours. After cooling the solvent was removed in vacuo, the residue dissolved in methylene chloride and washed three times with aqueous sodium carbonate and three times with brine. The organic layer was dried (Na₂SO₄) and evaporated in vacuo to give an oil methylene chloride. The product-containing fractions were combined and evaporated in vacuo to give an oil which was triturated with hexane and the evaporated in vacuo to give the title compound as a foam, yield 0.76 g.

Analysis %: Found: C,61.45; H,4.9; N,10.95; Calculated for $C_{19}H_{17}N_3O_5$: C,62.1; H,4.7; N,11.4*.

*¹H-N.m.r. indicated a trace (1/30 mole) of methylene chloride in the end product.

¹H-N.m.r. (CDCl₃): δ=8.5 (s, 1H); 8.2 (q, 1H); 8.02 (d, 1H); 8.00 (s, 1H); 7.6 (d, 1H); 7.3 (s, 1H); 6.8 (br s, 1H); 3.95 (s, H); 3.1 (br s, 4H); 2.8 (br s, 4H).

Preparation 4

7-Nitro-3-(6-nitroquinol-2-ylmethyl)-1,2,4,5-tetrahydro-3H-3-benzazepine

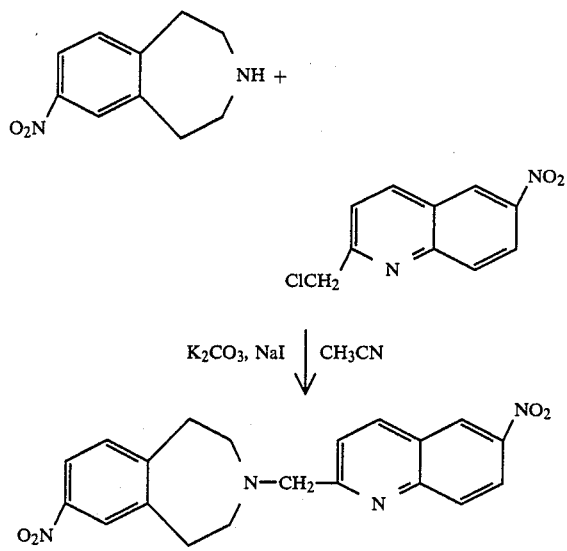

7-Nitro-1,2,4,5-tetrahydro-3H-3-benzazepine (0.35 g), 2-chloromethyl-6-nitroquinoline (0.4 g - see Chem. Pharm. Bull, 28, page 2441 [1980]), sodium iodide (0.27 g) and potassium carbonate (0.25 g) in acetonitrile were heated under reflux for 18 hours. The solvent was then removed in vacuo, the residue dissolved in methylene chloride and washed three times with aqueous sodium carbonate and twice with brine. The organic layer was dried (Na₂SO₄) and evaporated in vacuo to give an oil which was triturated with hexane to give the title compound, yield 0.61 g, m.p. 127°-130°.

Analysis %: Found: C,63.2; H,4.7; N,14.6; Calculated for C₂₀H₁₈N₄O₄: C,63.5; H,4.8; N,14.8.

Preparation 5

7-Amino-3-(5-aminobenzofur-2-ylmethyl)-1,2,4,5-tetrahydro-3H-3-benzazepine

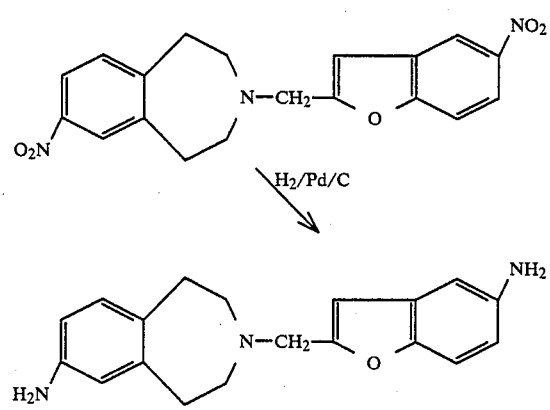

7-Nitro-3-(5-nitrobenzofur-2-ylmethyl)-1,2,4,5-tetrahydro-3H-3-benzazepine (0.74 g) was stirred at room temperature under a hydrogen atmosphere [344.7 kPa (50 p.s.i.)] in an ethanol solution containing 5% Pd/C for 2 hours. The catalyst was then removed by filtration and the filtrate evaporated in vacuo to give the title compound as a foam which was used without further purification, yield 0.58 g.

¹H-N.m.r. (CDCl₃): δ=7.25 (s, 1H); 6.9 (d, 1H); 6.85 (d, 1H); 6.7 (q, 1H); 6.5 (s, 2H); 6.45 (d, 1H); 3.85 (s, 2H); 2.9 (br s, 4H); 2.75 (br s, 4H).

Preparation 6

7-Amino-3-(6-aminoquinol-2-ylmethyl)-1,2,4,5-tetrahydro-3H-3-benzazepine

The title compound was prepared similarly to the procedure of Preparation 5 by the hydrogenation of 7-nitro-3-(6-nitroquinol-2-ylmethyl)-1,2,4,5-tetrahydro-3H-3-benzazepine using H₂/Pd/C in ethanol.

¹H-N.m.r. (CDCl₃) δ=7.9 (t, 2H); 7.6 (d, 1H); 7.2 (d, 1H); 6.95 (s, 1H); 6.9 (d, 2H); 6.5 (s, 1H); 6.45 (d, 1H); 3.95 (s, 2H); 3.9 (s, 4H); 3.7 (s, 4H).

We claim:

1. A compound of the formula:

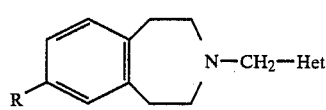

(A)

or a salt thereof, wherein "Het" is a group of the formula:

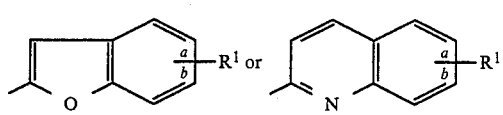

in which R¹ is attached to position "a" or "b" of the benzene ring and R and R¹, which are the same, are —NHSO₂(C₁–C₄ alkyl), —NH₂ or —NO₂.

2. A compound of the formula:

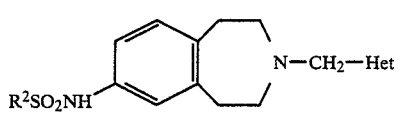

(I)

or a pharmaceutically acceptable salt thereof, wherein "Het" is a group of the formula:

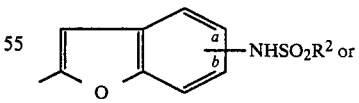

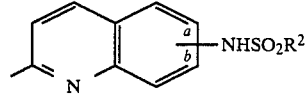

where each R², which is the same, is a C₁–C₄ alkyl group, the group —NHSO₂R² in "Het" being attached to position "a" or "b" of the benzene ring.

3. A compound as claimed in claim 2 which has the formula:

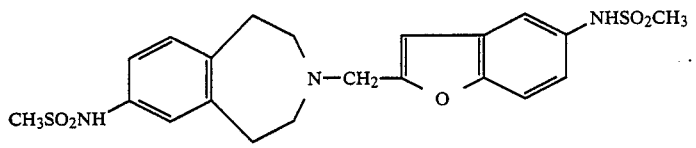

4. A compound as claimed in claim 2 which has the formula:

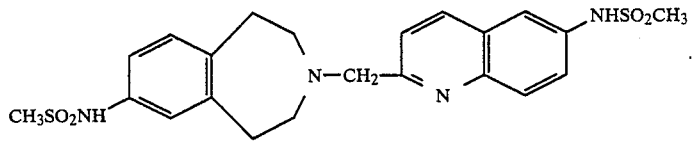

5. A pharmaceutical composition comprising an antiarrhythmic effective amount of a compound as claimed in claim 2 and a pharmaceutically acceptable diluent or carrier.

6. A pharmaceutical composition according to claim 5, wherein said compound is a compound of the formula

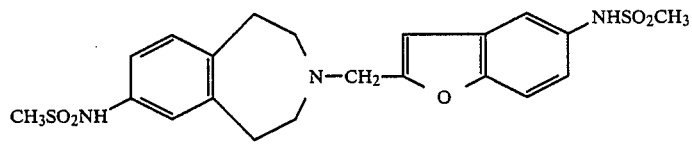

or a pharmaceutically acceptable salt thereof.

7. A pharmaceutical composition according to claim 5, wherein said compound is a compound of the formula

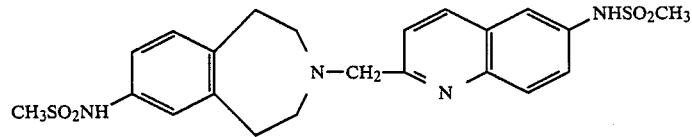

or a pharmaceutically acceptable salt thereof.

8. A method of treating cardiac arrhythmias in mammals comprising administering to a mammal in need of such treatment an antiarrhythmic effective amount of a compound as claimed in claim 2.

9. A method according to claim 8, wherein said compound is a compound of the formula

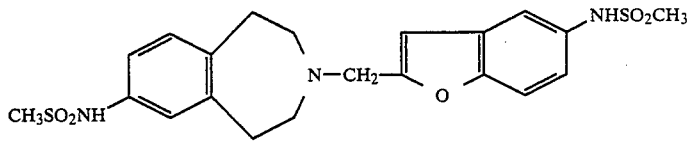

or a pharmaceutically acceptable salt thereof.

10. A method according to claim 8, wherein said compound is a compound of the formula

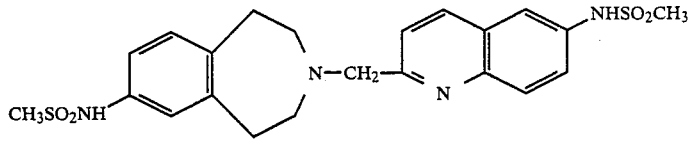

or a pharmaceutically acceptable salt thereof.

11. A method according to claim 8, wherein said mammal is a human.

12. A method according to claim 9, wherein said mammal is a human.

13. A method according to claim 10, wherein said mammal is a human.

* * * * *